(12) United States Patent
Moonen et al.

(10) Patent No.: US 10,537,751 B2
(45) Date of Patent: Jan. 21, 2020

(54) DEVICE FOR POSITIONING THE ENERGY-GENERATING MEANS OF AN ASSEMBLY FOR THE HEAT TREATMENT OF BIOLOGICAL TISSUES

(75) Inventors: Chretien Theophilus Willibrordus Moonen, Gradignan (FR); Rares Salomir, Chaponost (FR); Charles Mougenot, Bordeaux (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2376 days.

(21) Appl. No.: 11/587,801

(22) PCT Filed: Apr. 28, 2005

(86) PCT No.: PCT/EP2005/051935
§ 371 (c)(1),
(2), (4) Date: Jul. 15, 2008

(87) PCT Pub. No.: WO2005/107870
PCT Pub. Date: Nov. 17, 2005

(65) Prior Publication Data
US 2009/0012514 A1    Jan. 8, 2009

(30) Foreign Application Priority Data
Apr. 29, 2004   (FR) .................................... 04 04561

(51) Int. Cl.
*A61N 7/02* (2006.01)
*A61B 90/00* (2016.01)
(Continued)

(52) U.S. Cl.
CPC ................ *A61N 7/02* (2013.01); *A61B 90/50* (2016.02); *A61B 2017/00911* (2013.01); *A61B 2090/374* (2016.02)

(58) Field of Classification Search
CPC .............. A61N 2007/0091; A61N 7/02; A61N 2007/0082; A61N 2017/00911;
(Continued)

(56) References Cited

U.S. PATENT DOCUMENTS 5,136,742 A * 8/1992 Stebbins .............. A47C 19/045
5/610
5,291,890 A * 3/1994 Cline et al. ................... 600/411
(Continued)

FOREIGN PATENT DOCUMENTS

DE    197 45 400 C1    4/1999
FR    2823678 A1    10/2002
(Continued)

OTHER PUBLICATIONS

Gavrilov et al., "A Theoretical Assessment of the Relative Performance of Spherical Phased Arrays for Ultrasound Surgery," IEEE Transactions on Ultrasonics, Ferroelectrics, and Frequency Control, Jan. 2000, 47(1):125-139.

*Primary Examiner* — Thomas J Hong
*Assistant Examiner* — Helene Bor
(74) *Attorney, Agent, or Firm* — Sherry Austin (57) ABSTRACT

A device for positioning an energy-generating transducer probe a movement unit. The transducer probe may be configured for heat treatment of biological tissues and emits energy in one aiming direction which is located in an aiming plane. The movement unit is configured to alter the position of the transducer probe and, consequently, the aiming direction in the aiming plane around a target zone within the aiming plane.

19 Claims, 9 Drawing Sheets

(51) Int. Cl.
*A61B 90/50* (2016.01)
*A61B 17/00* (2006.01)

(58) Field of Classification Search
CPC ....... A61B 5/708; A61B 6/0435; A61B 90/50; A61B 17/2255; A61B 5/0555; G01R 33/4814
USPC ...................................... 601/3; 600/444, 447
See application file for complete search history.

(56) References Cited

U.S. PATENT DOCUMENTS

| | | | |
|---|---|---|---|
| 5,409,497 A * | 4/1995 | Siczek et al. | 600/407 |
| 5,443,068 A * | 8/1995 | Cline | A61B 5/0555 600/411 |
| 5,522,869 A | 6/1996 | Burdette et al. | |
| 5,526,814 A * | 6/1996 | Cline | A61B 17/2256 600/411 |
| 5,549,638 A * | 8/1996 | Burdette | 601/3 |
| 6,148,225 A | 11/2000 | Kestler et al. | |
| 6,475,150 B2 * | 11/2002 | Haddad | 600/448 |
| 6,506,154 B1 * | 1/2003 | Ezion et al. | 600/437 |
| 6,516,211 B1 | 2/2003 | Acker et al. | |
| 6,582,381 B1 * | 6/2003 | Yehezkeli et al. | 601/2 |
| 6,735,461 B2 * | 5/2004 | Vitek et al. | 600/411 |
| 6,778,848 B1 * | 8/2004 | Bechtold et al. | 600/411 |
| 7,379,769 B2 | 5/2008 | Piron et al. | |
| 7,494,466 B2 | 2/2009 | Chanhan et al. | |
| 8,905,036 B2 | 12/2014 | Moonen et al. | |
| 2003/0181806 A1 * | 9/2003 | Medan et al. | 600/411 |
| 2004/0081273 A1 * | 4/2004 | Ning | 378/37 |
| 2004/0176680 A1 | 9/2004 | Moonen et al. | |
| 2005/0080333 A1 * | 4/2005 | Piron | A61B 8/0825 600/417 |
| 2005/0107692 A1 * | 5/2005 | Li et al. | 600/430 |
| 2005/0143638 A1 * | 6/2005 | Johnson et al. | 600/407 |
| 2009/0012514 A1 | 1/2009 | Moonen et al. | |

FOREIGN PATENT DOCUMENTS

| | | |
|---|---|---|
| FR | 2823678 B1 | 10/2002 |
| JP | H08215208 A | 8/1996 |
| JP | 2000254139 A | 9/2000 |
| JP | 2003512103 A | 4/2003 |
| JP | 2003235863 A | 8/2003 |
| JP | 2003325510 A | 11/2003 |
| JP | 2004025175 A | 1/2004 |
| JP | 2004097534 A | 4/2004 |
| WO | WO 2003/059434 A3 | 7/2003 |

* cited by examiner

FIG_6

FIG_7

FIG_8

FIG_9

FIG_10

FIG_11

FIG_12

FIG_13

FIG_14

FIG_15

FIG_16

FIG_17

FIG_18

FIG.19

FIG_20

US 10,537,751 B2

DEVICE FOR POSITIONING THE ENERGY-GENERATING MEANS OF AN ASSEMBLY FOR THE HEAT TREATMENT OF BIOLOGICAL TISSUES

This application is a National Stage application of PCT/EP2005/051935, filed Apr. 28, 2005, which claims priority from French patent application FR 0404561, filed Apr. 29, 2004. The entire contents of each of the aforementioned applications are incorporated herein by reference.

The invention relates to the field of the treatment of biological tissues with hyperthermia, and more particularly the treatment of breast tissue.

Hyperthermia therapies are techniques commonly used to treat biological tissues locally. They consist of heating a target zone of biological tissue by means of an energy source (laser, microwave, radio frequency wave, ultrasound).

In general, local hyperthermia therapies allow medical interventions for which the invasive nature is reduced to a minimum. Among the types of energy used, focused ultrasound (FUS) is particularly interesting as it makes it possible to heat a target zone deep within the tissue in a noninvasive way.

The document FR 2,823,678 (published on Oct. 25, 2002) disclosed an assembly for heat treatment that makes it possible to control, in an automatic manner, the temperature in a target zone of the tissue to be treated. The unit comprises an ultrasound generator, a MRI imaging means for measuring and recording the spatial distribution of temperature in the target zone, and a control unit comprising means of point-by-point digital processing of the spatial distribution of temperature. The control unit controls the displacement in space of the ultrasound generator as a function of the distribution of temperature measured by the imaging means in such a way that the temperature in the target zone follows a temperature setting profile.

Within the framework of the treatment of the breast, the positioning of the energy-generating means is delicate because the breast is near vital organs such as the pleura, the lungs and the heart. It is important to avoid a situation in which the necrosis generated by the increase in temperature in the tissues extends to these vital organs.

The problem resolved by the invention is to propose a positioning device for the energy-generating means which is adapted to the treatment of the breast and which minimizes the risk of damage to the organs nearby.

The invention resolves this problem by means of an assembly for the heat treatment of the breast, comprising:
  an energy-generating means adapted to emit energy in an aiming direction included in an aiming plane,
  a means of support adapted to maintain the body of a patient in a position in which the coronal plane of the body of the patient extends approximately parallel to the aiming direction while the breast of the patient cuts across the aiming direction,
  characterized in that it comprises in addition a positioning device that includes a means of movement adapted to alter the position of the energy-generating means around the breast of the patient in the aiming plane, the aiming plane extending approximately parallel to the coronal plane.

With such a positioning assembly, the body of a patient to be treated is maintained in a position in which the coronal plane of the body of the patient extends approximately parallel to the aiming direction and in which the breast of the patient cuts across this aiming direction. The energy emitted in the aiming direction is propagated only within the breast and never reaches the vital organs.

Within the framework of this invention, "coronal plane" means a plane passing through the center of gravity of the body which divides the body into an anterior portion and a posterior portion. The coronal plane (or frontal plane) extends perpendicular to the sagittal plane (the sagittal plane, containing the spinal column, being the symmetry plane of the body which delimits the body into a left portion and a right portion).

The means of movement alters the position of the energy-generating means in the aiming plane around the breast to adjust the position of the focal point of the energy-generating means in the target zone to be treated and to alter the distribution of energy over time as a function of, for example, the spatial distribution of temperature.

In such a configuration, the risk of accumulating energy in the organs at risk, such as the pleura, the lungs or the heart, is reduced since the ultrasonic energy is propagated within the breast only.

Other characteristics and advantages, which will arise from the description which follows, are purely illustrative and nonrestrictive and must be read in the context of the attached figures, which include:

FIG. 1, which represents diagrammatically the various components of an assembly for the heat treatment of the breast, FIG. 2, which represents the positioning of the energy-generating means in the form of a focused ultrasonic transducer with respect to the breast of the patient, FIGS. 3, 4 and 5, which are perspective, top and side views, respectively, of the focused ultrasonic transducer, FIG. 6, which represents diagrammatically the spatial coverage between two successive aimings of the focused ultrasonic transducer, FIGS. 7, 8 and 9, which represent the acoustic field intensity curves generated by the focused ultrasonic transducers exhibiting various shapes, FIGS. 10, 11 and 12, which represent diagrammatically the distribution of the ultrasound-generating elements on the active surface of the transducer in front, side and top views, respectively, FIG. 13, which represents diagrammatically the means of support adapted to maintain the body of a patient in a heat treatment assembly in conformity with the invention, FIG. 14, which represents diagrammatically a positioning device for the energy-generating means in conformity with the invention, FIG. 15, which represents diagrammatically the energy-generating means in the form of a focused ultrasonic transducer equipped with a means of interface intended to encourage the propagation of the ultrasound in the breast, FIG. 16, which represents diagrammatically an example of the electronic architecture of a multichannel generator intended to supply a focused ultrasonic transducer, FIG. 17, which represents diagrammatically an impedance matching circuit between a generator supply channel and an ultrasound-generating element, FIG. 18, which represents diagrammatically the positioning of the energy-generating means as well as the positioning of the MRI reception antenna inside the means of support provided to maintain the patient, FIG. 19, which represents a top view of the means of support of FIG. 13 more precisely, FIG. 20, which represents diagrammatically a top view of the component means of the positioning device of FIG. 14, these means of positioning being arranged beneath the means of support of FIG. 19.

Figure 1:
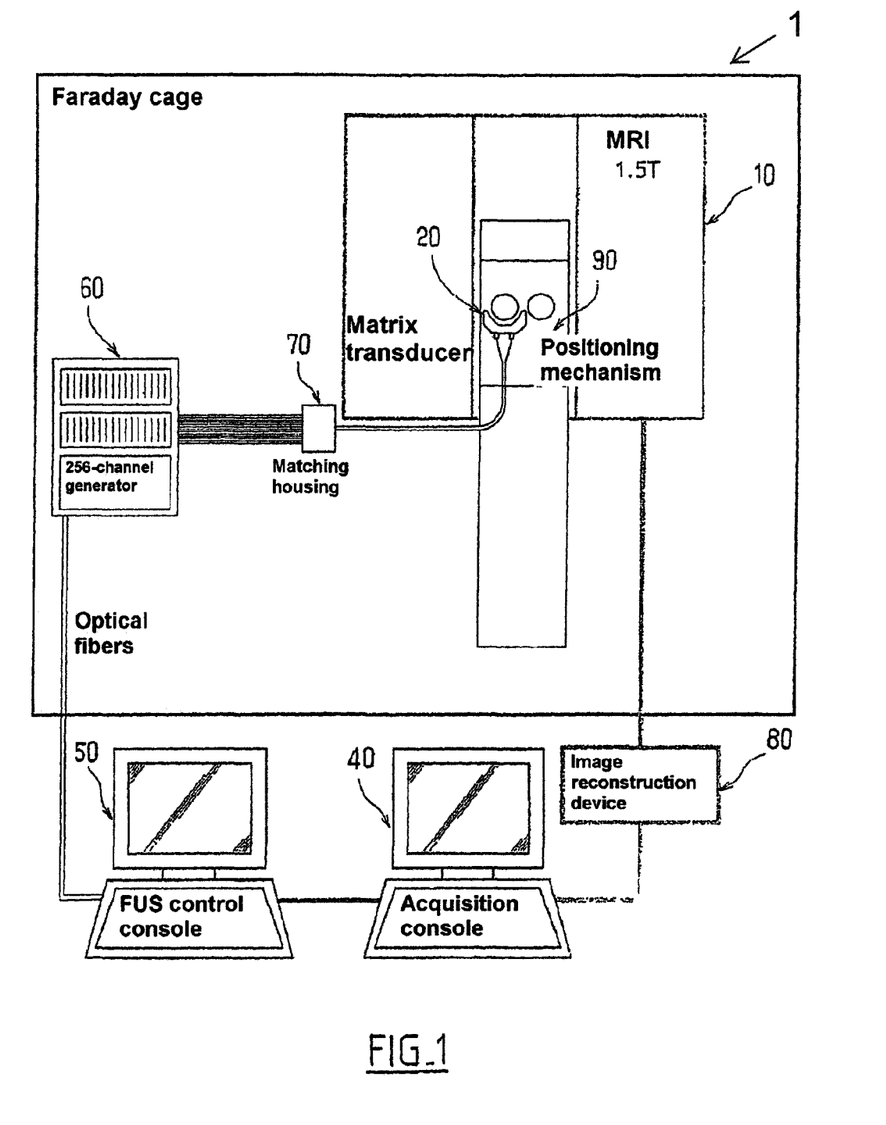

In FIG. 1, the heat treatment assembly 1 represented comprises a MRI imaging apparatus containing a magnet 10. The assembly 1 comprises energy-generating means in the form of a focused ultrasonic transducer 20 and a multichannel generator 60 intended to supply the transducer 20. The multichannel generator 60 (which comprises at least eight sinusoidal supply channels) is connected to the transducer 20 via an electronic impedance matching device 70.

The assembly 1 also comprises an image reconstruction device 80, an acquisition unit 40 that includes a central processing unit capable of receiving input data arriving from the image reconstruction device 80, and a control unit 50 that is capable, as a function of the data provided by the acquisition unit 40, to control the multichannel generator 60 and the movement system 90 to alter the distribution of the energy emitted by the transducer 20 as a function of the distribution of temperature measured by the MRI imaging apparatus.

The MRI imaging apparatus provides simultaneously a three-dimensional map of the temperature of the area of interest and an anatomical map with a spatial resolution on the order of a millimeter, a precision on the order of 1° C. and a temporal resolution on the order of 1 second.

The multichannel generator comprises 256 channels, each channel being intended to supply an ultrasound-generating element of the probe 20. The signals generated in each channel are transmitted via 50Ω coaxial cables by means of the electronic impedance matching device 70 to the probe 20. The electronic impedance matching device 70 also acts as a low-pass filter which allows the use of the focused ultrasound and the MRI simultaneously without the interference described in the document U.S. Pat. No. 6,148,225 (published on Nov. 14, 2000).

The measurements acquired inside the magnet 10 are converted into images by an image reconstruction device 80 and are transmitted to the acquisition unit 40. The acquisition unit 40 carries out a fast Fourier transform and filters on the acquired image and displays the image thus treated on a display. The doctor can visualize the image on the display and locate a tumor to be treated.

Temperature maps that include the target zone to be heated are generated by the MRI imaging apparatus. The data are transferred in real time by a high-speed network connection from the acquisition unit 40 to the control unit 50 which is dedicated to the control of the focused ultrasound-generating means. The control unit 50 includes a suitable program for implementing a control algorithm for the multichannel generator 60 and the movement system 30. This algorithm is capable of calculating, as a function of the temperature maps provided by the MRI imaging apparatus, the coordinates and the intensity of the ultrasound aimings to be carried out with a view to generating an increase in heat necessary to obtain a necrosis. The control algorithm controls the multichannel generator 60 and the positioning device 90 so that the temperature in the target zone follows a desired profile.

The control signals emitted by the control unit 50 are transmitted to the multichannel generator 60 via fiber-optic conductors.

At the end of the treatment, images from a diffusion MRI or from a T2-weighted MRI with or without a contrast agent make it possible to carry out a follow-up of the patient to verify the size of the necrosis generated as well as its change over time.

Focused Ultrasonic Transducer

The disadvantage of circular probes is the elongated shape of the focal point along the aiming axis. During the deposit of a large quantity of energy in order to generate a large increase in temperature or to treat a large volume, the necrosis propagates towards the transducer up to the surface of the skin.

Figure 6:
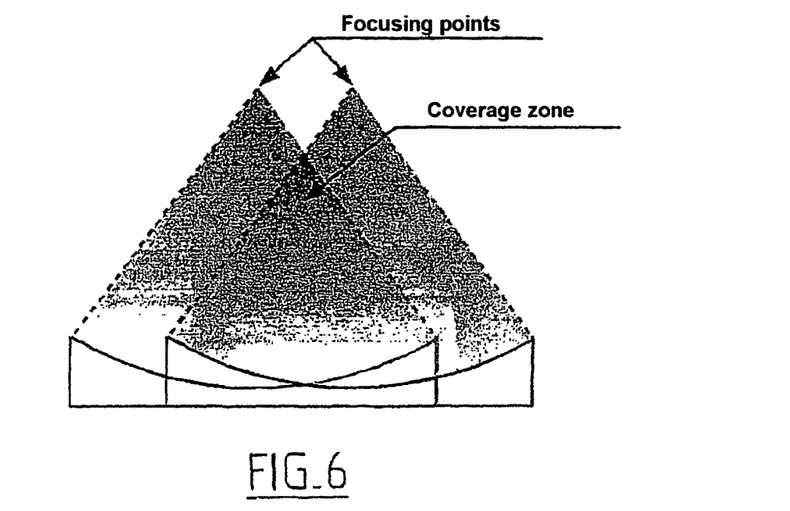

As can be seen in FIG. 6, during the emission of several close consecutive pulses, part of each beam overlaps. Thus by making several consecutive pulses across the entire surface of a disk an ellipsoid is obtained for which the length ratio is equal to the length ratio of the focal point. This energy accumulation effect along the ultrasound propagation axis can be dangerous when the necrosis extends to the vital nearby organs.

As for the ultrasonic transducer 20, it is particularly adapted to treat tumors of the breast.

Figure 2:
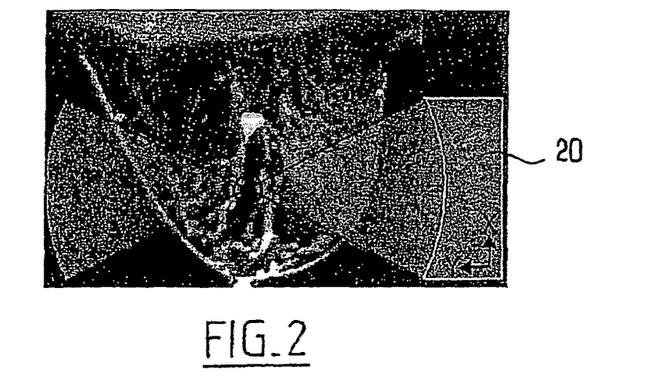

In FIG. 2, the transducer 20 is intended to be positioned with respect to the breast of the patient to be treated so that the aiming direction of the ultrasound extends approximately parallel to the coronal plane of the patient. In such a configuration, the risk of accumulating energy in the organs at risk, such as the pleura, the lungs or the heart, is reduced since the ultrasonic energy is propagated within the breast only.

Figure 3:
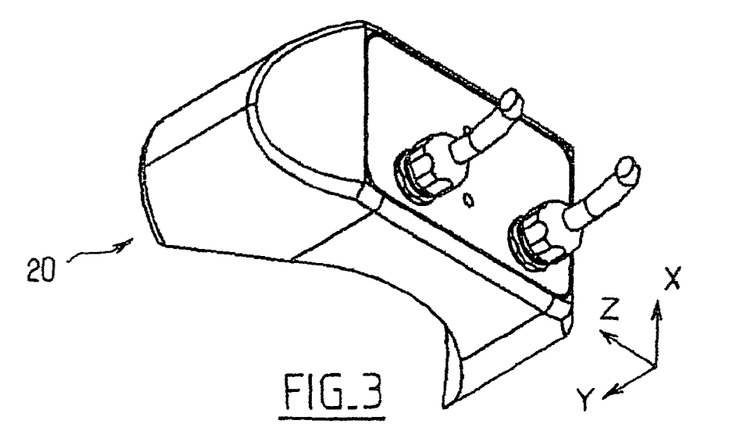
Figure 4:
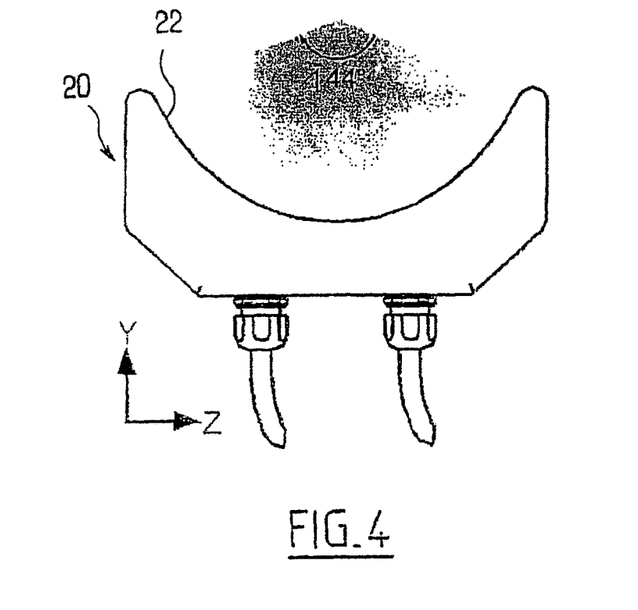
Figure 5:
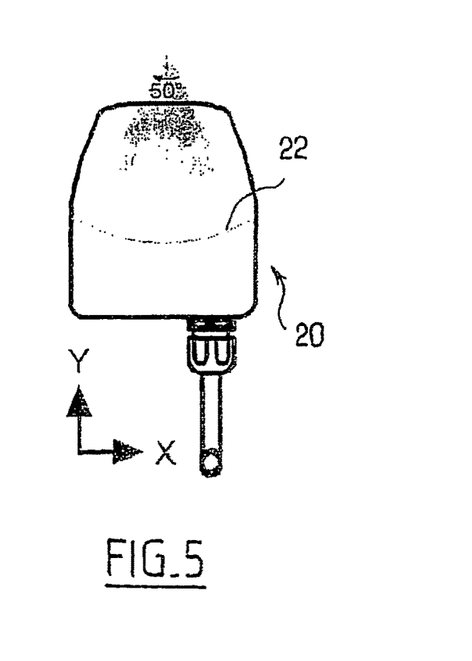

As illustrated in FIGS. 3 to 5, the transducer 20 has an active ultrasound emission surface 22 of a generally concave and elongated shape. More precisely, the active surface 22 of the transducer is a portion of a sphere whose aperture in a first direction is greater than 90 degrees while the aperture in a second direction perpendicular to the first direction is less than 90 degrees. The active surface 22 has a radius of curvature of 8 cm and is elongated in the direction of the aiming plane. Thus the transducer 20 makes it possible to treat zones located up to 8 cm deep within the body.

FIG. 4 is a top view of the transducer, in the YZ aiming plane. In this plane, the active surface 22 has an aperture of 144 degrees. FIG. 5 is a side view of the transducer, in the YX plane perpendicular to the YZ aiming plane. In this plane, the active surface has an aperture of 50 degrees. To obtain sufficient power the active surface is 68 cm$^2$.

Additionally, by increasing the aperture of the transducer, it is possible to decrease the length of the focal point. Its arrangement in the coronal plane at the periphery forms almost a half-arc. The circle half-arc is excluded to prevent a face of the probe from radiating on the other face, which could cause its self-destruction. The aperture of the transducer in the XY plane is 144° (FIG. 4). To have a transducer that is sufficiently compact, that is to say, with an active surface of 68 cm$^2$, the aperture of the probe in the Xz plane is reduced to 50° (FIG. 5). This makes it possible to position the transducer near the body as shown in FIG. 2.

The fact of increasing the aperture of the transducer in one direction makes it possible to reduce the length of the focal point. Thus, with an aperture of 1440 the length of the focal point is near the wavelength, which here is 1 mm.

Figure 18:
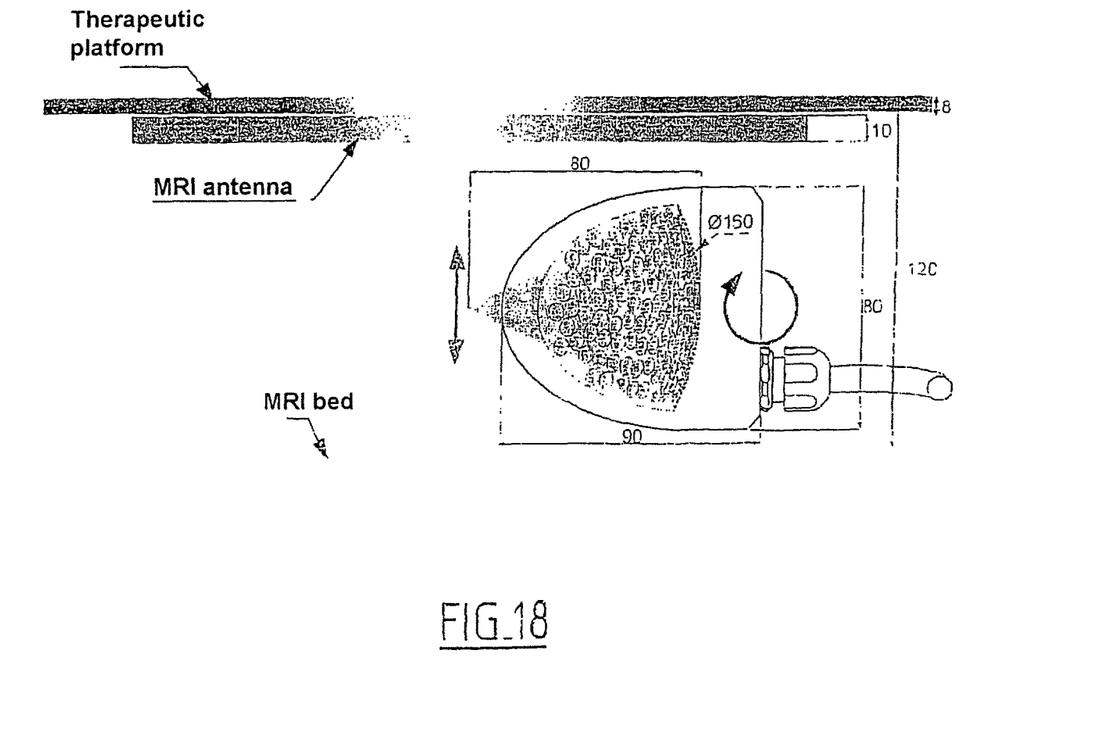

The elongated shape of this transducer makes it possible in addition to optimize the volume within the MRI imaging apparatus. Indeed, the diameter of a MRI is currently limited to a radius of 60 cm. This is already preventing some obese patients from receiving MRI diagnoses. With a therapeutic platform in the MRI, the space available for the patient is further reduced. For these reasons, it is essential to optimize the thickness of this platform, which depends primarily on the size of the transducer as shown in FIG. 18. The transducer must have an emitting surface of at least 68 cm$^2$ to have sufficient power and must have a minimal height in the platform; it is preferable that it has a maximum aperture and the densest possible positioning of elements. However, the aperture of the transducer must not exceed 180° or the transducer would emit upon itself.

Figure 10:
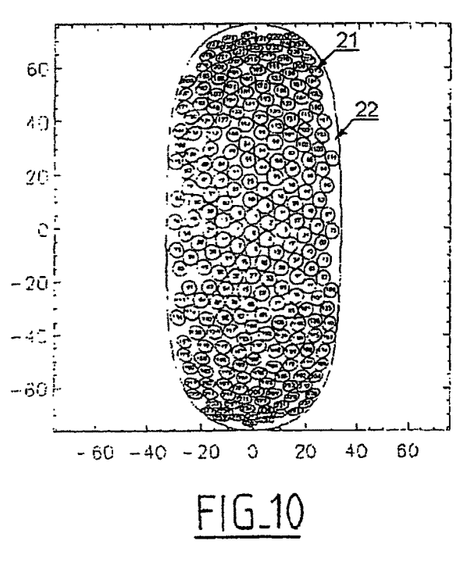
Figure 11:
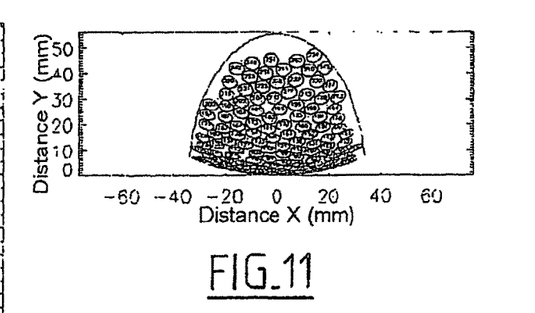
Figure 12:
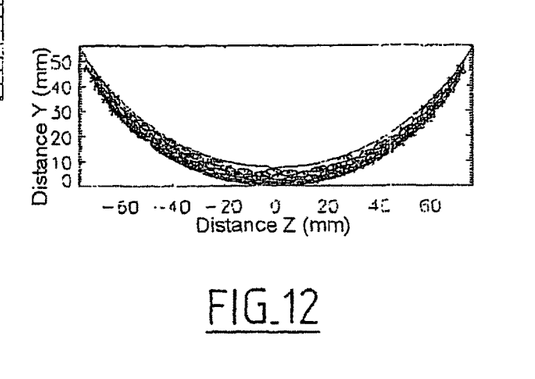

As illustrated in FIG. 10, the active surface 22 of the transducer 20 is covered with a matrix network of ultrasound-generating elements and contains 256 circular generating elements capable of emitting ultrasound in the direction of a focal point P when the transducer 20 is supplied by the generator 60.

When the transducer is supplied by a multichannel generator, via its connections, the ultrasound-generating elements 21 are capable of emitting at a frequency of approximately 1.5 MHz. The focal point P has dimensions on the order of the wavelength, that is to say, approximately 1 mm. The acoustic pressure generated at the focal point can be adjusted by altering the amplitude and the phase shift of the supply signals from the multichannel generator 60.

The matrix network formed by the ultrasound-generating elements 21 is compact and asymmetrical. The fact that the matrix network is compact means that each generating element 21 is contiguous with at least two other elements to minimize the surface occupied by the generating elements. A generating element is considered to be contiguous with another generating element if these elements are located at a distance of less than 2 mm from one other. The fact that the matrix network is asymmetrical means that the generating elements 21 are distributed in an asymmetrical manner on the active surface 22.

An iterative algorithm places the elements one by one, according to the following principle:

By knowing the coordinates of the first n elements, a program calculates the positions of the elements contiguous to at least two elements among the n elements to minimize the surface occupied by the n+1 element. Without considering the minimum distance of 2 mm, the calculations can be carried out in the same manner as for scattered matrix networks by positioning the elements randomly. However, a space between the elements is necessary to avoid creating electric arcs between the connections of the elements and to avoid mechanical friction between the elements vibrating in phase opposition. This inter-element space has been selected to be equal to 0.4 mm in the case of the transducer described herein.

Among the configurations that minimize the surface occupied, a program makes it possible to select the one that exhibits the smallest degree of symmetry.

According to a first process which can be implemented by this program, the degree of symmetry is evaluated by searching, for each plane containing the Y axis, for the number of symmetrical elements between them with respect to one of these planes. Since certain elements can be almost symmetrical to one another without being completely symmetrical, an autocorrelation function makes it possible to quantify in a continuous manner the degree of symmetry more so than in a discrete manner. Thus, the element distribution retained is that for which each plane containing the Y axis returns a minimum symmetry autocorrelation. The fact of suppressing the axes of symmetry makes it possible to decrease the lobes of symmetry which are the most constraining in the use of the matrix network.

Figure 7:
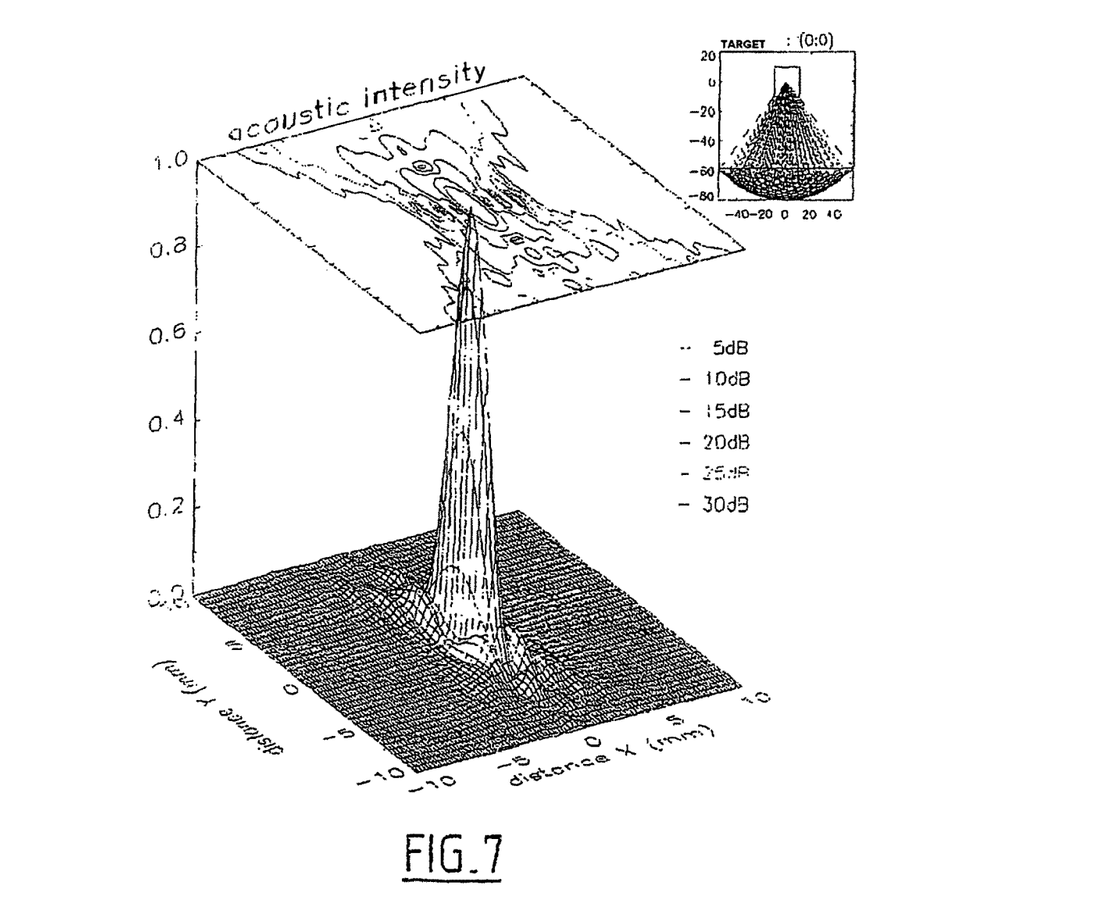
Figure 8:
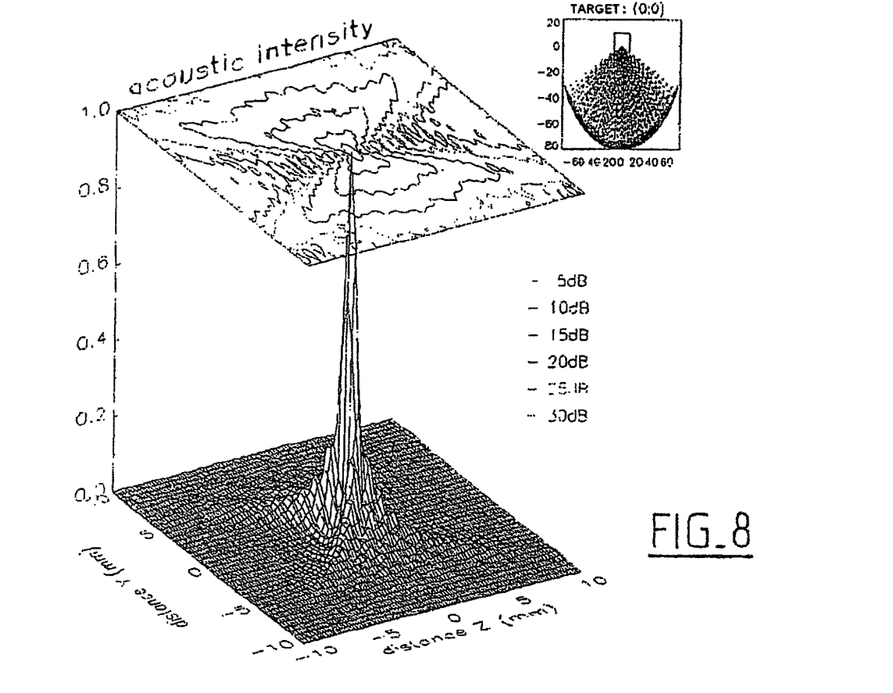
Figure 9:
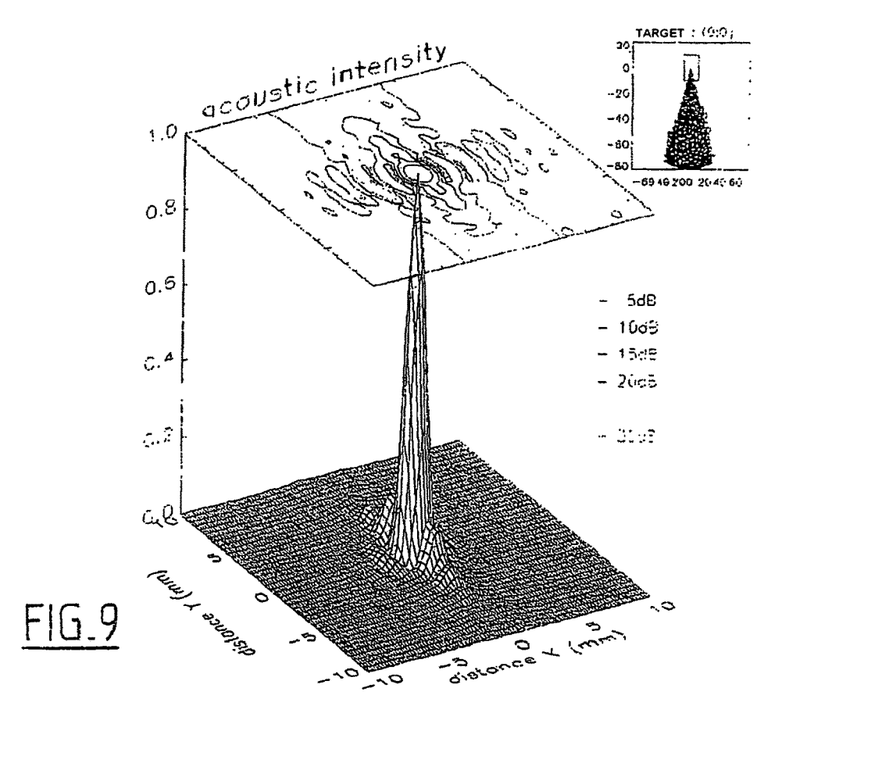

According to a second iterative process, more rigorous but requiring a much longer calculation time, simulations of the acoustic field are carried out for each configuration that minimizes the surface occupied as illustrated in FIGS. 7, 8 and 9. This process makes it possible to determine exactly the configuration that minimizes the secondary lobes generated by the transducer.

However, the first process also makes it possible to suppress the layer distribution on the transducer since when two elements have the same coordinates on the Y axis, they are exactly symmetrical to each other for one of the planes passing through the Y axis. From this property arises a minimization of the network lobes.

These processes lead to several different distributions according to the choice of the position of the first element. To remove this uncertainty, it is possible to compare each distribution of 256 elements in order to choose the one that presents the best performance in terms of focusing quality.

The matrix network thus obtained presents the advantages of focusing quality of scattered semi-random networks as described in the document by Gravillov, L. R. et al., "A theoretical assessment of the relative performance of spherical phased arrays for ultrasound surgery", IEEE transactions on ultrasonic, ferroelectrics and frequency control, January 2000, 47, 125-139, while remaining compact. Compactness is an advantage for use inside a MRI imaging apparatus where the space available for the transducer is limited by the dimensions of the magnet.

The matrix network of generating elements 21 makes it possible to adjust electronically the position of the focal point P with a precision of 7.5 mm in all directions around the natural focusing point. Moreover, the compact, asymmetrical distribution of the elements 21 makes it possible to preserve the secondary intensity lobes that are less than 8% of the intensity at the focusing point, regardless of its position in the region described previously.

FIGS. 7, 8 and 9 represent intensity curves of the acoustic field generated by focused ultrasonic transducers of various shapes. These figures make it possible to compare the acoustic field generated by a transducer of elongated shape with the field generated by a traditional transducer.

FIG. 7 shows the intensity of the acoustic field in the XY plane in a window of 20×20 mm$^2$ around the focal point P of a circular matrix transducer represented in the upper left corner. This transducer, containing 256 identical elements, has a focal distance of 80 mm and a 55 mm aperture radius, which leads to an aperture of 86 degrees. The calculation of the intensity of the acoustic field was carried out for an emission frequency of the generating elements of 1.5 MHz in a medium with a velocity of propagation of 1540 m/s. This calculation yields a focal point of dimensions 0.76× 0.76×3.5 mm$^3$.

FIG. 8 shows the intensity of the acoustic field in the YZ plane in a window of 20×20 mm$^2$ around the focal point P of the transducer described in relation to FIG. 3 and represented in the upper left corner. This transducer also has a focal distance of 80 mm and functions at 1.5 MHz in a medium with a velocity of propagation of 1540 m/s. This calculation yields a focal point of dimensions 1.28×1.6 mm$^2$ in the YZ plane.

FIG. 9 shows the intensity of the acoustic field in the XY plane in a window of 20×20 mm$^2$ around the focal point P of the transducer described in relation to FIG. 3 and represented in the upper left corner. With the same calculation parameters as those of FIG. 7, a focal point of dimensions 0.48×1.28×1.6 mm$^3$ is obtained.

Moreover, to be able to move the aiming center of the transducer up or down mechanically (double right arrow in FIG. 18), it is more judicious to pivot the transducer according to the circular arrow than to translate the transducer. The translation would require more space for the platform and would make it impossible to reach the part of the breast next to the rib cage. To have a maximum freedom of rotation of the transducer along the blue axis, it is cut in such a way that its cross-section corresponds to a half ellipse. In three dimensions, it corresponds to the intersection of an elliptic cylinder with a sphere. A triangular cross-section would allow greater rotation but the rounded corners are necessary for the ergonomics and the rigidity of the transducer.

Transducer Positioning Device

The electronic control of the signals is fast and precise. However, electronic adjustment of the position of the point is limited and alone does not allow it to reach all areas of the breast. For this reason, a mechanical centering of the transducer on the center of the tumor is necessary.

Figure 13:
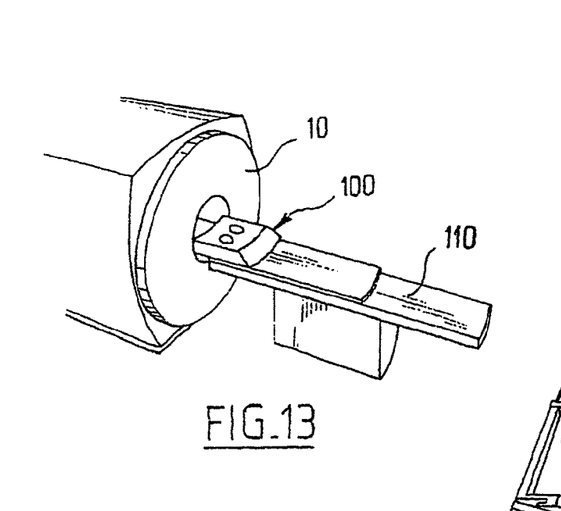

In FIG. 13, the assembly for the heat treatment of the breast represented comprises a means of support 100 adapted for maintaining the body of a patient in a position in which the coronal plane of the body of the patient extends approximately parallel to the aiming direction while the breast of the patient cuts across the aiming direction.

The means of support are formed of a platform adapted to be positioned on the bed 110 of the MRI imaging device 10 on which the patient lies. When the platform 100 is positioned on the bed 110, it extends approximately parallel to the bed by making a space between the platform and the bed. The space made between the platform and the bed is intended to house the energy-generating means comprising the focused ultrasonic transducer and a positioning device for the transducer.

Figure 19:
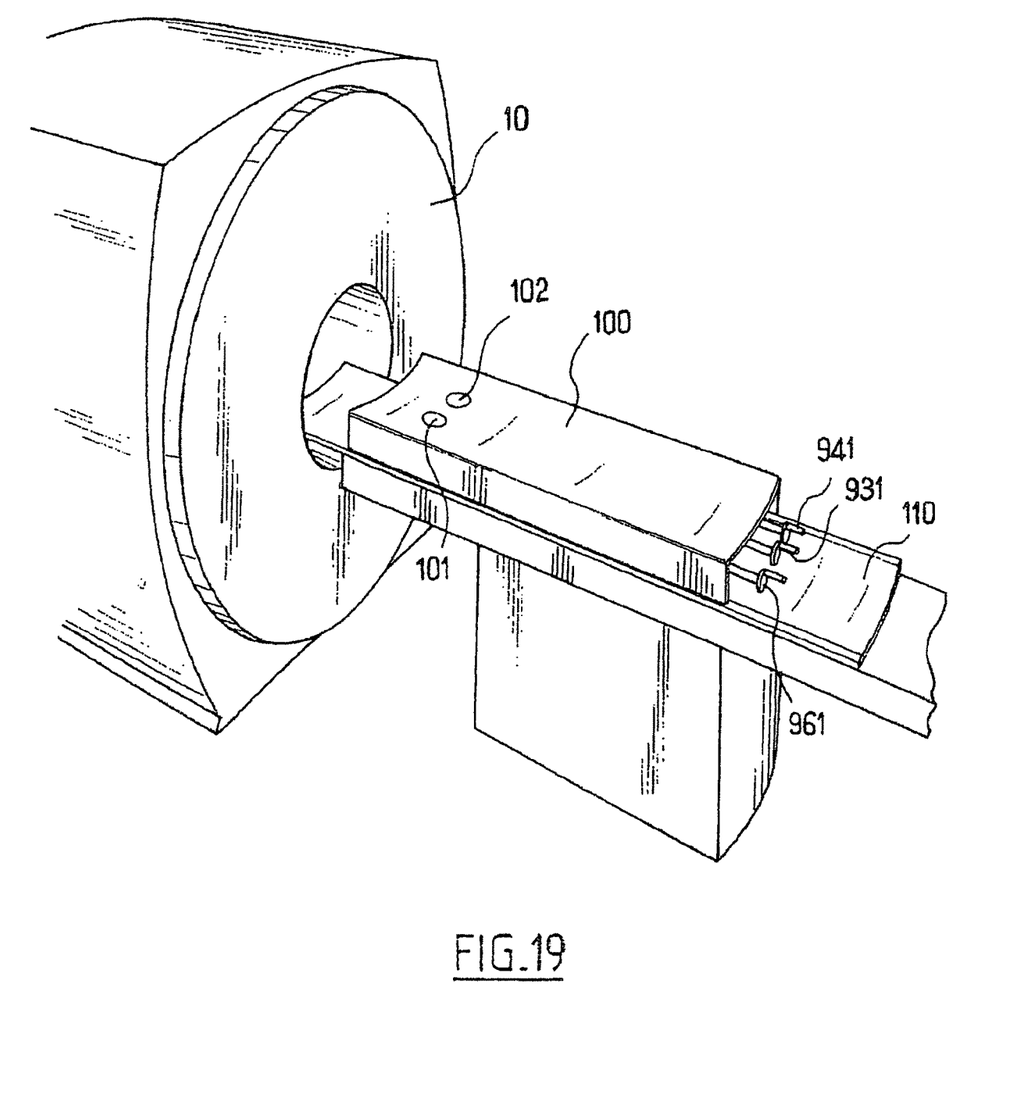

As can be seen more precisely in FIG. 19, the platform 100 comprises two openings 101 and 102 arranged in such a way that when the patient lies face down on the bed 110 of the MRI imaging apparatus 10, the breasts of the patient are introduced into the openings 101 and 102 for the purpose of treatment. The ergonomic platform 100 makes it possible to ensure the comfort of the patient while preventing the weight of the patient from resting on the transducer located under the platform.

Figure 14:
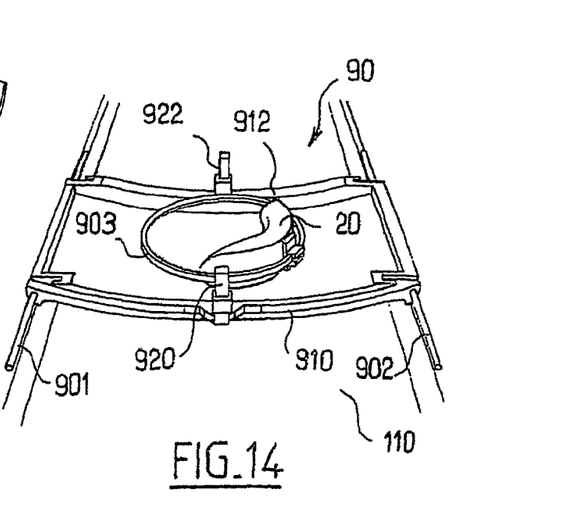

The positioning device 90 is represented in FIG. 14. The means of movement are adapted to maintain the energy-generating means 20 in a position in which these generating means 20 emit energy in an aiming direction parallel to the coronal plane of the patient. The positioning device is also adapted to alter the position of the energy-generating means 20 in an aiming plane parallel to the coronal plane of the patient, around the breast of the patient.

The movement device comprises two rods 901 and 902 intended to be positioned along the lengthwise edges of the bed 110 of the MRI imaging apparatus on which the patient is positioned and two guide rails 910 and 912 which at their extremities rest upon and slide along the rods 901 and 902 and extend across the direction of the bed 110. Each of the two rails 910 and 912 receives a post 920 and 922, respectively) that extends in a general direction perpendicular to the bed 110 of the MRI imaging apparatus and can slide along its rail 910 and 912. The two posts 920 and 922 support a generally ring-shaped frame 903 on which the energy-generating means are mounted. The ring-shaped frame 903 delimits a central aiming area in which the breast of the patient is received.

The energy-generating means comprise a focused ultrasonic transducer 20 having an active surface of a generally spherical shape. The transducer is mounted on the ring-shaped frame 903 in such a way that the aiming plane of the transducer 20 extends in the plane of the ring-shaped frame 903 and the natural focal point of the spherical active surface of the transducer 20 is positioned in the center of the frame 903.

Figure 20:
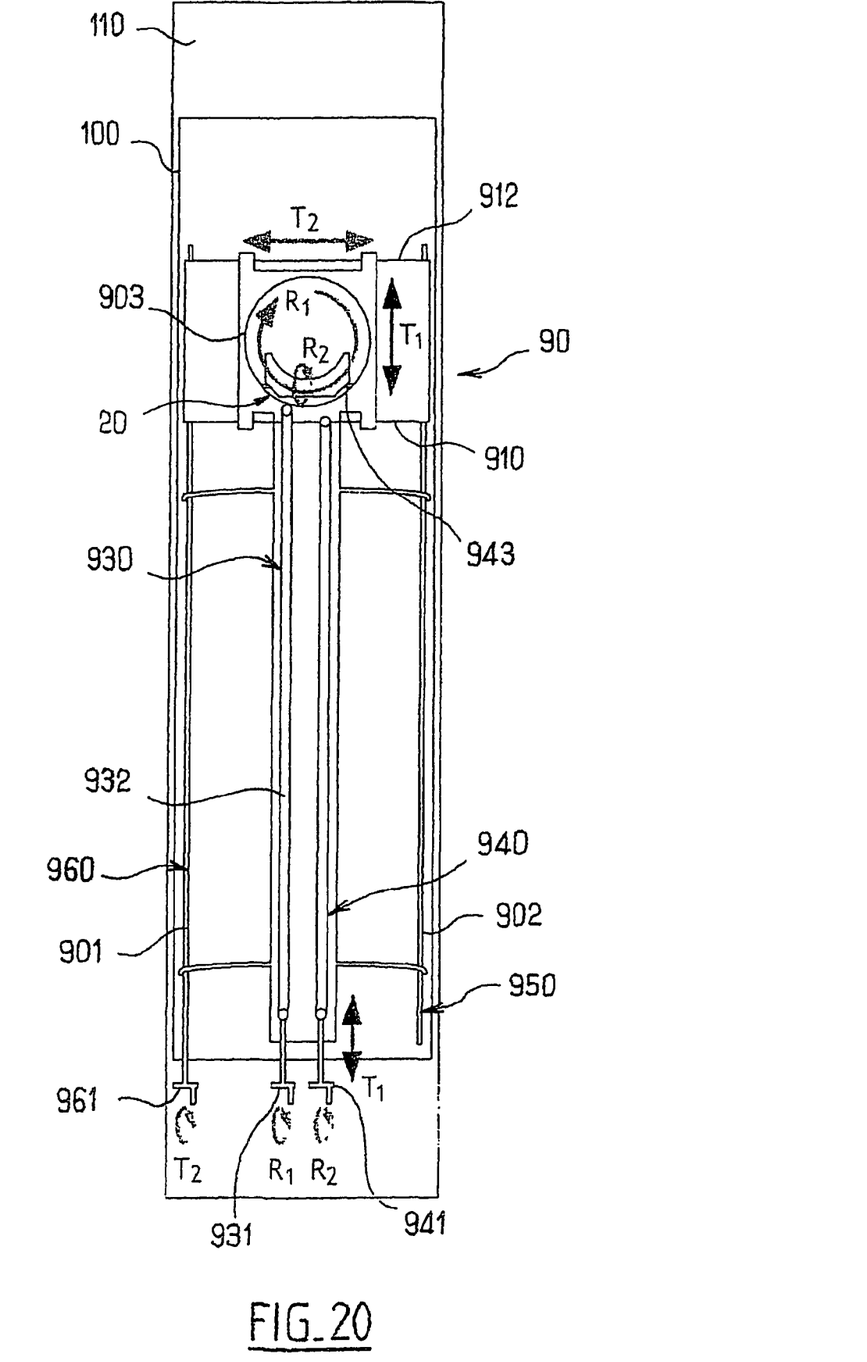

As can be seen more precisely in FIG. 20, the positioning device 90 comprises the first means of movement 930 adapted to alter the position of the frame 903. By virtue of these means of movement 930, the frame 903 can be rotated around its center (rotation $R_1$), in the aiming plane, which makes it possible to alter the position of the transducer 20 in the aiming plane around the breast of the patient. For this purpose, the first positioning device 930 comprises a mechanical system of belts and gears. The driving belt 932 of the first positioning device extends in the lengthwise direction of the bed and is controlled by a crank 931.

In addition, the positioning device includes a second means of movement 940 adapted to alter the orientation of the aiming plane, in the form of an axis of rotation 943 extending in the plane of the frame 903. The energy-generating means 20 are assembled in a rotary fashion with respect to the frame 903 on the axis 943. The energy-generating means 20 can thus tilt slightly with respect to the coronal plane of the patient (rotation $R_2$). The second means of movement 940 make it possible to tilt the aiming plane with a clearance between +40 degrees and −40 degrees with respect to the frame and thus with respect to the coronal plane of the patient. This characteristic offers the possibility of an additional adjustment of the position of the focal point P of the ultrasonic transducer.

The energy-generating means 20 are comprised advantageously of an ultrasonic transducer with rounded contours, which make it possible to alter its position and its orientation without the transducer coming into contact with the bed 110 or the means of support 100.

In addition, the positioning device includes a third means of translation movement 950 comprising the rods 901 and 902 that extend along the lengthwise edges of the bed 110. The assembly formed by the transducer 20, the ring-shaped frame 903, the posts 920 and 922 and the rails 910 and 912 can be moved along the rods 901 and 902 in the lengthwise direction of the bed 110 (translation $T_1$). For this purpose, it suffices for an operator to turn the cranks 931 and 941 to pull or push the assembly in the lengthwise direction of the bed 110.

The positioning device includes a fourth means of translation movement 960 comprising guide rails 910 and 912. The assembly formed by the transducer 20, the ring-shaped frame 903 and the posts 920 and 922 can slide along the rails 910 and 912 following a transverse direction of the bed 110 (translation $T_2$). Thus, the assembly can be positioned along the width of the bed of the MRI imaging apparatus. The movement device 960 makes it possible to adapt the position of the transducer 20 according to the position of the breast of the patient to be treated. For this purpose, the means of translation movement 960 include a rod 901 at the end of which a crank 961 is mounted. An operator can control the rotation of the rod 901 by turning the crank 961. The rotation of the rod 901 controls a belt extending in a transverse direction with respect to the bed 110 (not represented) to which is attached the assembly formed by the transducer 20, the ring-shaped frame 903 and the posts 920 and 922. The belt translates the assembly along the rails 910 and 912.

The transducer 20 can thus be moved along 2 translation axes and 2 rotation axes by virtue of the four means of movement 930, 940, 950 and 960 described previously. In this way it is possible to center the aiming on any area within the breast while maintaining the aiming direction approximately parallel to the coronal plane. The means of movement 930, 940 and 960 are controlled remotely by the cranks 931, 941 and 961 located at the foot of the bed. These means of movement thus make it possible to adjust the position of the transducer 20 without altering the position of the patient on the bed 110.

The positioning device and the means of support offer an extremely simple installation since it suffices to place them directly on the bed of the MRI imaging apparatus.

In addition, the positioning device described takes up less space which enables it to be installed beneath the means of support, thus preserving a maximum amount of space in the MRI imaging apparatus 10 for the patient.

Means of Interface for Encouraging Ultrasound Propagation

The energy emitted by the energy-generating means outside the body of the patient is, in part, transmitted towards the area to be treated inside the body of the patient and is, in part, lost because of the interfaces between media of different acoustic densities.

Figure 15:
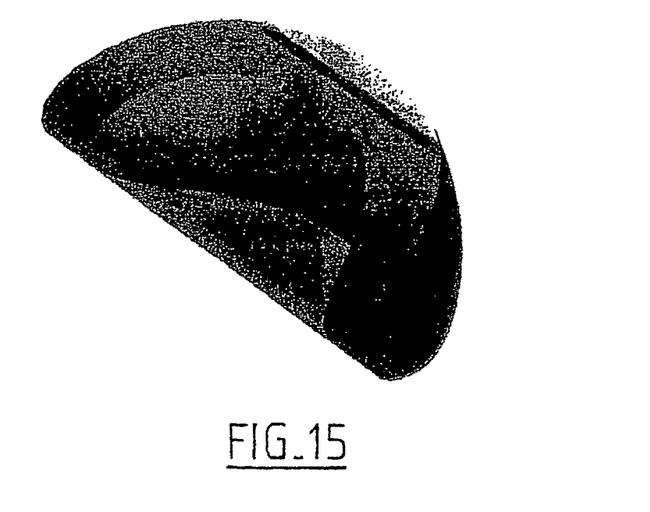

A solution to simplify the transmission of the ultrasonic waves towards the target zone to be treated is represented in FIG. 15.

FIG. 15 represents a focused ultrasonic transducer. The active surface of the transducer is covered with a deformable membrane intended to come in contact with the skin of the patient to be treated. The space created between the active surface of the transducer and the membrane is filled with water. This characteristic encourages the propagation of the ultrasonic waves generated by the transducer towards the interior of the body of the patient. Indeed, the waves emitted by the ultrasound-generating elements are propagated in a medium having an approximately constant acoustic density.

To suppress the effects of cavitation in the water, the water can be degassed beforehand with a vacuum pump.

Multichannel Supply Generator

Figure 16:
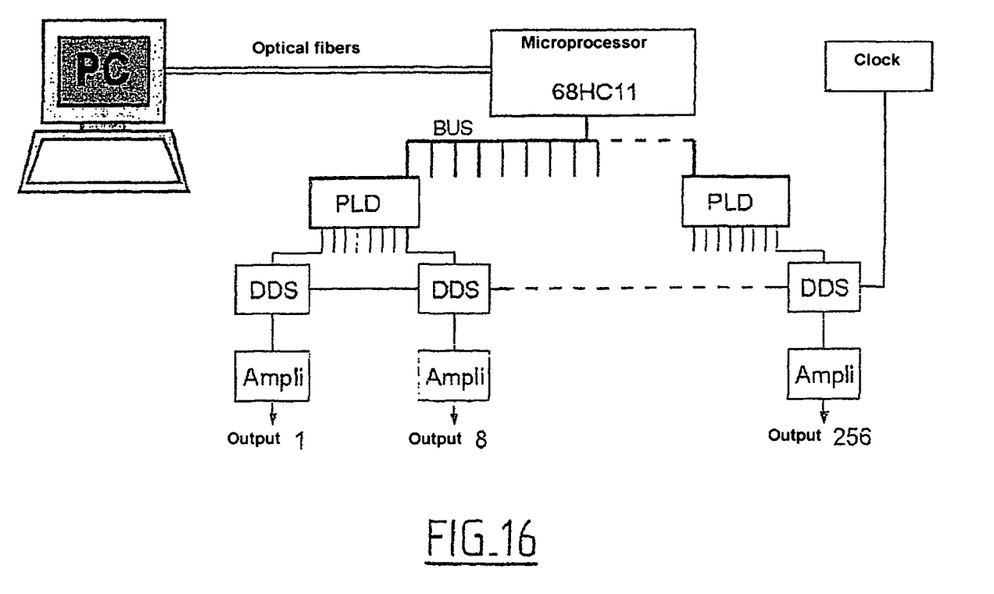

FIG. 16 represents diagrammatically an example of the electronic architecture of a multichannel generator intended to supply a focused ultrasonic transducer. The multichannel generator is controlled by a control unit of the heat treatment assembly. The multichannel generator 60 includes at least 256 sinusoidal supply channels capable of being controlled independently of each other in amplitude and in phase and exhibiting a switching time lower than 100 ms.

In FIG. 16, the control unit includes a MOXA C104H board making it possible to increase the speed of the serial port from 115,200 Kb/s to 460,800 Kb/s. The control unit transmits information about frequencies, phases and amplitudes to the multichannel generator which are used by the generator to generate corresponding control signals. With such a system, the control signals can be completely redefined every 65 ms.

For hydraulic pistons with a speed of 2 m/s, the movement of the focal point of the focused ultrasonic transducer is limited to a point every 2 seconds with a maximum distance of 4 mm between each point. On the other hand, combined with a matrix transducer, this generator makes it possible to heat 15 independent-points each second.

The treatment assembly comprises an optical fiber bundle making it possible to connect the control unit, which is located outside the Faraday cage surrounding the MRI imaging apparatus, to the multichannel generator located inside the Faraday cage. The optical fiber bundle allows high-speed transmission over long distances and constitutes an excellent protection with respect to electromagnetic interference. The optical fiber bundle makes it possible to transmit the information generated by the control unit through the Faraday cage without permitting electromagnetic disturbance arising from the exterior. The connection between the control unit and the generator is thus ensured without interfering with the operation of the MRI imaging apparatus.

In addition, the generator is designed to function inside a MRI room. The boards which it contains have been selected to generate weak electromagnetic radiation. Thus, the installation of the multichannel generator requires the installation of two optical fibers only.

The multichannel generator includes a 68HC11 microprocessor. The function of the microprocessor is to distribute the data to the programmable logic device (PLD) on the 32 boards which generate 8 sinusoids each. The programmable logic devices then will transmit information about phases and frequencies to the direct digital synthesizers (DDS) and information about power to the amplifiers. The direct digital synthesizers (DDS) are arranged in parallel and are capable of generating supply signals for the matrix network of ultrasound-generating elements of the transducer according to the phase and frequency information which they receive. The direct digital synthesizers ensure fast and precise switching signals. This characteristic represents an improvement with respect to traditional ultrasonic signal generators with delay lines which do not exceed a phase precision greater than ±5°. The amplitudes of the sinusoids are then adjusted by variable-gain amplifiers.

The use of a clock that is common to all the direct digital synthesizers ensures synchronized switching of all the outputs states of the multichannel generator. This characteristic makes it possible to avoid transient states in which the ultrasound signals generated by the ultrasonic transducer are unfocused. The common clock improves safety for the patient by maintaining the focusing of the signals.

The definition of the signals by the control unit is made by the transmission to the microprocessor of the multichannel generator of a file containing data according to the following order:

4 optional bytes that code the frequency common to all the ultrasound-generating elements and whose value is:

$$F = 24 \text{ MHz} \times \frac{\text{Number coded in 32 bits}}{2^{32}}$$

The frequency F is thus defined between 0 and 24 MHz with a precision of +3 MHz.

512 bytes defining in 2 bytes the respective phase φ of each signal in such a way that:

$$\phi = 360° \times \frac{\text{Number coded in 16 bits}}{2^{12}}$$

Coding in 512 bytes makes it possible to adjust all the phases between 0 and 3600 with a precision of +0.04°.

256 bytes defining the output power of each channel according to the relationship:

$$P = 4 \text{ W} \times \frac{\text{Number coded in 8 bits}}{2^8}$$

Output power can thus vary up to 4 W with a precision of +8 mW.

The communications protocol is in XMODEM format in half-duplex connection mode. Each 128-byte packet transmitted is sent by the receiver which controls reception by a cyclic redundancy check (CRC) character coded in 1 byte. In this way the control unit can transmit a file defining frequencies, phases and amplitudes every 22 ms.

The architecture of the 256-channel generator has the following advantages:

speed in redefining control signals,
simultaneous signal changes,
weak electromagnetic radiation,
precision in the definition of output sinusoids,
a secure data exchange,
portability.

Impedance Matching Device

Figure 17:
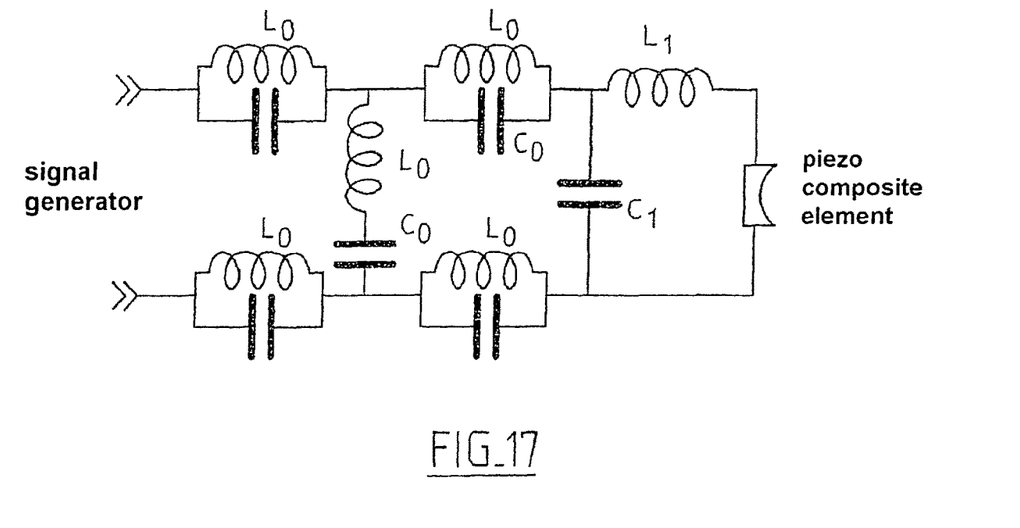

On each of the 256 channels, an electronic impedance matching device, represented in FIG. 17, is inserted between the output of the multichannel generator and the piezoelectric energy-generating element. The 256 circuits are placed in a housing located at the foot of the magnet in order to be as close as possible to the energy-generating means without obstructing access to the center of the magnet.

The impedance matching device has two roles.

On the one hand, the impedance matching device makes it possible to adapt the impedance of the piezoelectric energy-generating elements to 50Ω.

For this purpose, the device represented in FIG. 17 comprises inductive $L_1$ and capacitive $C_1$ components assembled into a low-pass filter. The inductance and capacity values are selected in the following manner:

$$C_1 = \frac{1}{50 \; \Omega \omega} \sqrt{\frac{50 \; \Omega}{Z_R} - 1}$$

$$L_1 = \frac{Z_R}{\omega} \sqrt{\frac{50 \; \Omega}{Z_R} - 1} - \frac{Z_I}{\omega}$$

wHere $Z_R$ and $Z_I$ are the real part and the imaginary part of the electric impedance of a piezoelectric energy-generating element. With such inductance and capacity values, the electric impedance seen by the multichannel generator is set at 50Ω.

The electronic matching devices allow an optimal transfer of energy arriving from the generator via the 50Ω coaxial cable. The proximity of the electronic impedance matching devices to the probe is required in order not to have an inductance $L_1$ of too great a value not functioning at a high frequency and generating too much loss.

On the other hand, the impedance matching device limits interference from the MRI imaging apparatus (field gradients) on the signal generator and also from the ultrasonic signals on the NMR signal. For this purpose, the components $L_1$ and $C_1$ create a second-order low-pass filter. However, the behavior of the filter at high frequency is limited. For this reason, a network of notch filters resonating at 64 MHz=$(2\pi\sqrt{L_0 C_0})^{-1}$ is inserted between the output of the multichannel generator and the low-pass filter comprising the inductive $L_1$ and capacitive $C_1$ components in order to attenuate the signals at this frequency by a factor of 200.

The invention claimed is:

1. An assembly for heat treatment of a breast of a patient, comprising:
   an ultrasonic transducer configured to emit energy in an aiming direction included in an aiming plane; and
   a platform configured to maintain a body of the patient in a position in which a coronal plane of the body of the patient extends approximately parallel to the aiming direction while the breast of the patient cuts across the aiming direction;
   a bed; and
   a positioner that includes a frame that supports the ultrasonic transducer, the positioner further including a mechanical movement unit having movable rods extending along a length of the bed and movable guide rails extending across the bed, the movable rods being approximately parallel to the coronal plane of the body,
   wherein a first movable rod of the movable rods is configured to move the ultrasonic transducer along the length of the bed and across the bed,
   wherein a second movable rod of the movable rods is configured to rotate the ultrasonic transducer for rotating the aiming plane around a rotation axis extending through the coronal plane of the body,
   wherein a third of the movable rods is configured to tilt the aiming plane with respect to the coronal plane, and
   wherein a portion of two of the first, second and third movable rods are directly coupled to the frame.

2. The assembly according to claim 1, wherein the mechanical movement unit is further configured to alter one of an aiming plane position and an orientation of the aiming plane.

3. The assembly according to claim 1, wherein the mechanical movement unit is further configured to alter an orientation of the aiming plane by tilting of the aiming plane with a clearance ranging between +40 degrees and −40 degrees.

4. The assembly according to claim 1, wherein the second movable rod is configured to rotate the frame around a center of the frame.

5. The assembly according to claim 1, wherein the mechanical movement unit includes a driving belt activated by gears controlled by an activation unit, the activation unit being arranged at a distance with respect to the ultrasonic transducer.

6. The assembly according to claim 5, wherein the activation unit comprises a crank.

7. The assembly according to claim 1, wherein the ultrasonic transducer is a focused ultrasonic transducer that includes an active surface for emitting ultrasound, the active surface having a concave and elongated shape.

8. The assembly according to claim 7, wherein the active surface of the ultrasonic transducer is a portion of a sphere having an aperture of greater than 90 degrees in a first direction and less than 90 degrees in a second direction perpendicular to the first direction.

9. The assembly according to claim 7, wherein the active surface of the ultrasonic transducer is covered with ultrasound-generating elements forming a matrix network.

10. The assembly according to claim 9, wherein the matrix network formed by the ultrasound-generating elements is asymmetrical.

11. The assembly according to claim 1, comprising a signal generator configured to supply the ultrasonic transducer with supply signals, and a controller configured to control the signal generator to generate the supply signals, the controller being connected to the signal generator by optical transmission elements capable of transmitting control information from the controller to the signal generator.

12. The assembly according to claim 1, comprising a signal generator configured to supply the ultrasonic transducer with supply signals, the signal generator including multiple direct digital synthesizers (DDS) arranged in parallel and configured to generate the supply signals for a matrix network of ultrasound-generating elements of the ultrasonic transducer according to phase and frequency information.

13. The assembly according to claim 1, further comprising a multichannel electric generator, including at least 8 sinusoidal supply channels, configured to be controlled independently of each other in amplitude and in frequency and exhibiting a switching time lower than 100 ms.

14. The assembly of claim 1, wherein the rotation axis passes through a center of the frame that supports the ultrasonic transducer and is perpendicular to the coronal plane of the body.

15. The assembly of claim 1, wherein the mechanical movement unit is further configured to alter a position of the ultrasonic transducer by translating the positioner that includes the ultrasonic transducer in a plane parallel to the platform in a direction along a width of the patient.

16. The assembly of claim 1, wherein the mechanical movement unit is further configured to alter a position of the ultrasonic transducer by translating the positioner that includes the ultrasonic transducer in a plane parallel to the platform in a direction perpendicular to the length of the patient.

17. An assembly for heat treatment of a breast of a patient, comprising:
   an ultrasonic transducer configured to emit energy in an aiming direction included in an aiming plane; and
   a platform configured to maintain a body of the patient in a position in which a coronal plane of the body of the patient extends approximately parallel to the aiming direction while the breast of the patient cuts across the aiming direction;
   a bed; and
   a positioner that includes a frame that supports the ultrasonic transduce, the positioner further including a mechanical movement unit having movable rods extending along a length of the bed and movable guide rails extending across the bed, the movable rods being approximately parallel to the coronal plane of the body,
   wherein a first movable rod of the movable rods is configured to move the ultrasonic transducer along the length of the bed and across the bed,
   wherein a second movable rod of the movable rods is configured to rotate the ultrasonic transducer for rotating the aiming plane around a rotation axis extending through the coronal plane of the body,
   wherein a third of the movable rods is configured to tilt the aiming plane with respect to the coronal plane,
   wherein a portion of two of the first, second and third movable rods are directly coupled to the frame, and
   wherein the ultrasonic transducer includes a deformable membrane for covering an active surface of the ultrasonic transducer, contacting the breast and forming a space between the ultrasonic transducer and the deformable membrane, the space between the ultrasonic transducer and the deformable membrane being filled with water.

18. An assembly for heat treatment of a breast of a patient, comprising:
   an ultrasonic transducer configured to emit energy in an aiming direction included in an aiming plane; and
   a platform configured to maintain a body of the patient in a position in which a coronal plane of the body of the patient extends approximately parallel to the aiming direction while the breast of the patient cuts across the aiming direction;
   a bed; and
   a positioner that includes a frame that supports the ultrasonic transducer, the positioner further including a mechanical movement unit having movable rods extending along a length of the bed and movable guide rails extending across the bed, the movable rods being approximately parallel to the coronal plane of the body,
   wherein a first movable rod of the movable rods is configured to move the ultrasonic transducer along the length of the bed and across the bed,
   wherein a second movable rod of the movable rods is configured to rotate the ultrasonic transducer for rotating the aiming plane around a rotation axis extending through the coronal plane of the body,
   wherein a third of the movable rods is configured to tilt the aiming plane with respect to the coronal plane, and
   wherein the mechanical movement unit includes cranks located at ends of the first, second and third movable rods, the first, second and third movable rods extending in the space from a position near the ultrasonic transducer to the outer position outside the space near an end of the bed, and the first, second and third movable rods are parallel to the coronal plane of the body and extend lengthwise along the bed.

19. An assembly for heat treatment of a breast of a subject, comprising:
   an ultrasonic transducer configured to emit energy in an aiming direction included in an aiming plane;
   a platform configured to maintain a body of the subject in a position in which a coronal plane of a body of the patient extends approximately parallel to the aiming direction while the breast of the subject cuts across the aiming direction;
   a bed; and
   a positioner that includes a frame that supports the ultrasonic transducer, the positioner further including a mechanical movement unit having movable rods extending along a length of the bed and movable guide rails extending across the bed, the movable rods being approximately parallel to the coronal plane of the body,
   wherein a first movable rod of the movable rods is configured to move the ultrasonic transducer along the length of the bed and across the bed,
   wherein a second movable rod of the movable rods is configured to rotate the ultrasonic transducer for rotating the aiming plane around a rotation axis extending through the coronal plane of the body,
   wherein a third of the movable rods is configured to tilt the aiming plane with respect to the coronal plane,
   wherein a portion of two of the first, second and third movable rods are directly coupled to the frame, and
   wherein the ultrasonic transducer includes an active surface and a deformable membrane that covers the active surface for contacting the breast and forming a space between the ultrasonic transducer and the deformable membrane, the space between the ultrasonic transducer and the deformable membrane being filled with water.

* * * * *